US011395940B2

(12) United States Patent
Lianides et al.

(10) Patent No.: US 11,395,940 B2
(45) Date of Patent: Jul. 26, 2022

(54) SYSTEM AND METHOD FOR PROVIDING GUIDED AUGMENTED REALITY PHYSICAL THERAPY IN A TELEMEDICINE PLATFORM

(71) Applicants: Christopher Lee Lianides, Aliso Viejo, CA (US); Terrell Brian Marshall, Jr., Sacramento, CA (US); Aditya Ramchandra Nadkarni, Cupertino, CA (US); Michelle Minh Hien Nguyen, Dallas, TX (US); Ekta Anil Shahani, Santa Clara, CA (US)

(72) Inventors: Christopher Lee Lianides, Aliso Viejo, CA (US); Terrell Brian Marshall, Jr., Sacramento, CA (US); Aditya Ramchandra Nadkarni, Cupertino, CA (US); Michelle Minh Hien Nguyen, Dallas, TX (US); Ekta Anil Shahani, Santa Clara, CA (US)

( * ) Notice: Subject to any disclaimer, the term of this patent is extended or adjusted under 35 U.S.C. 154(b) by 170 days.

(21) Appl. No.: 17/065,303

(22) Filed: Oct. 7, 2020

(65) Prior Publication Data
US 2022/0105389 A1 Apr. 7, 2022

(51) Int. Cl.
*G09G 5/00* (2006.01)
*A63B 24/00* (2006.01)
(Continued)

(52) U.S. Cl.
CPC ...... *A63B 24/0075* (2013.01); *A63B 24/0062* (2013.01); *A63B 24/0087* (2013.01);
(Continued)

(58) Field of Classification Search
CPC ....... A63B 24/0075; G06T 7/251; G06T 7/70; G06T 19/006
See application file for complete search history.

(56) References Cited

U.S. PATENT DOCUMENTS 8,715,176 B2  5/2014 Lemme
9,600,934 B2  3/2017 Odessky et al.
(Continued)

OTHER PUBLICATIONS

Anderson et al., YouMove: Enhancing Movement Training with an Augmented Reality Mirror, UIST'13, 2013, pp. 311-320 (Year: 2013).*

*Primary Examiner* — Charles Tseng
(74) *Attorney, Agent, or Firm* — The Dobrusin Law Firm, PC (57) ABSTRACT

The present invention provides a method, a system, and a computer storage medium to provide a guided augmented-reality physical exercise in a virtual platform comprising of initiating the exercise to provide a live stream of the user's body image and poses on the user interface; selecting an exercise wherein a reference skeleton image is animated on the user interface showing target poses for the user to mimic; capturing and tracking the user poses to provide captured body frame data; analyzing such data using a pose detection model to provide analyzed body motion frame data for the creation of a superposed skeleton image that dynamically tracks and moves with the user body poses on the user live stream; determining whether the body poses match the target poses using a pose matching algorithm; and indicating whether such match existed by changing appearance of one or more portions of the superposed skeleton image.

20 Claims, 5 Drawing Sheets

(51) Int. Cl.
  *A63B 71/06* (2006.01)
  *G06T 7/246* (2017.01)
  *G06T 19/00* (2011.01)
  *G10L 15/26* (2006.01)
  *G06T 7/70* (2017.01)
(52) U.S. Cl.
  CPC .......... *A63B 71/0622* (2013.01); *G06T 7/251* (2017.01); *G06T 7/70* (2017.01); *G06T 19/006* (2013.01); *G10L 15/26* (2013.01); *A63B 2024/0068* (2013.01); *A63B 2024/0096* (2013.01); *A63B 2071/0636* (2013.01); *A63B 2071/0647* (2013.01)

(56) References Cited

U.S. PATENT DOCUMENTS

| | | |
|---|---|---|
| 2018/0276895 A1 | 9/2018 | Hodge |
| 2018/0374383 A1* | 12/2018 | Thielen ................. G06T 19/006 |
| 2019/0295438 A1* | 9/2019 | Rubinstein ............... G09B 5/06 |
| 2020/0005544 A1* | 1/2020 | Kim ........................ G06T 13/40 |
| 2020/0047055 A1* | 2/2020 | Ward ...................... G06F 3/016 |
| 2021/0065452 A1* | 3/2021 | Gazioglu ................ G06T 11/60 |

* cited by examiner

SYSTEM AND METHOD FOR PROVIDING GUIDED AUGMENTED REALITY PHYSICAL THERAPY IN A TELEMEDICINE PLATFORM

FIELD OF THE INVENTION

The present invention relates generally to a system and a method for providing guided augmented reality physical therapy in a telemedicine platform, and more particularly, a system and a method for providing augmented reality physical therapy with real-time analysis of a user's body movements and other biofeedback information while being guided by a live but remotely located health care provider during a video call session.

BACKGROUND OF THE INVENTION

Roughly 100 million adult Americans are living with a musculoskeletal injury every single day, but about 65% of physical therapy (PT) patients do not follow up after their injury. Lengthy commutes pose a significant challenge to patients, especially in suburban, rural, and under-served areas, which can be painful or even dangerous while injured. Patients that unable to make it to PT are left with options like: living with their pain and not going to the provider; hire a home nurse for PT, which may not be covered by their insurance, and as a last resort, they can try to follow videos or articles online but risk further injury if they learn & perform exercises incorrectly.

Because of the risk and cost of these existing solutions, telemedicine is the most practical path forward. However, telemedicine has its own share of gaps. Current telemedicine use cases are limited to treating simple conditions like the flu because their user experiences are similar to Skype® and Facetime®. These platforms are not leveraging advanced technology to address the specific needs of physical therapy patients. Building a solution for PT requires enabling communication based on the patient's body movement to keep patients safe without a physical therapist in the same room.

As described in detail below, the present invention provides a solution for PT that enable a physical therapist in a video call session to provide guided augmented reality physical therapy by remotely guiding the patient's body movements using real-time analysis of the patient's body movements and other biofeedback information.

SUMMARY OF THE INVENTION

One embodiment of the present invention is a computer implemented method to provide a guided augmented-reality physical exercise in a virtual platform ("ARPE") implemented in a system having a central server, a database, a user interfacing device, a provider interfacing device, each having one or more processors and a memory; the method comprising executing on the processors the steps of: initiating the ARPE wherein: a user uses the user interfacing device to communicate with a provider during the ARPE, wherein the user interfacing device further includes a user video capturing device, a user audio capturing device, a user interface controlled by a user frontend application; the provider uses the provider interfacing device to communicate with the user during the ARPE, wherein the provider interfacing device further includes a provider video capturing device, a provider audio capturing device, and a provider interface controlled by a provider frontend application; the user interfacing device and the provider interfacing device are communicating video data and audio data via an interactive communication API over a network wherein the video data includes a user live stream showing the user body image and the user poses captured by the user video capturing device and displayed on the user interface and the provider interface; selecting an exercise wherein a reference skeleton image is rendered and animated on the user interface by the user frontend application showing target poses, wherein the target poses demonstrate the exercise's desired body movements thereby allowing user to mimic the target poses during the exercise with the user poses; capturing and tracking the user poses during the exercise using the user video capturing device and the user frontend application to provide a captured body frame data for each video frame of the user live stream during the exercise; analyzing the captured body frame data using a pose detection model to provide an analyzed body motion frame data comprising markers and confidence scores, wherein the markers include two dimensional X and Y coordinates; creating a superposed skeleton image onto the user body image displayed on the user live stream using the user frontend application, a pose rendering library, and a pose matching algorithm to process the analyzed body motion data in order to obtain normalized vectors of the X and Y coordinates, thereby allowing the superposed skeleton image to dynamically tracks and moves with the user body poses; determining whether the body poses match the target poses based upon similarity scores derived from the normalized vectors of the X and Y coordinates and the confidence scores processed by the pose matching algorithm; and indicating whether a match existed between the body poses and the target poses by changing appearance of one or more portions of the superposed skeleton image.

Other embodiments include, without limitation, a computer-readable medium that includes instructions that enable a process to implement on or more aspects of the disclosed methods as well as a system having a processor, memory, and applications/program configured to implement one or more aspects of the disclosed methods of the present invention.

DESCRIPTION OF THE DRAWINGS

The features and inventive aspects of the present invention will become more apparent upon reading the following detailed description, claims, and drawings, of which the following is a brief description:

DETAILED DESCRIPTION

The Augmented Reality Physical Therapy System

Figure 1:
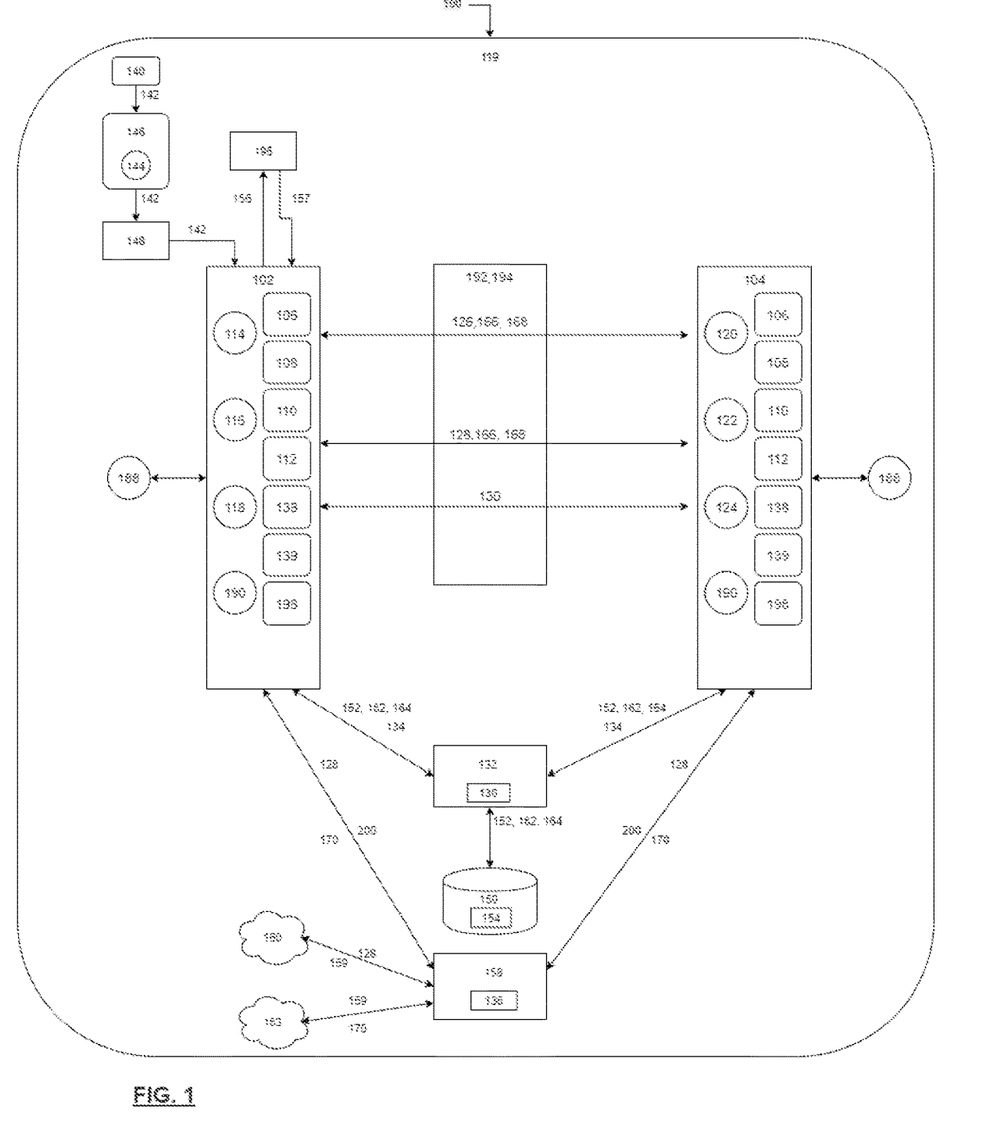
FIG. 1 is a schematic view of an augmented-reality system in accordance with embodiments of the present invention.

Referring to FIG. 1, the present invention provides a system 100 for providing guided augmented reality physical therapy with real-time analysis of a user's body movements and other biofeedback information while performing predetermined exercises and being guided by a live but remotely located health care provider during a video call session (hereinafter referred to as "ARPT"). FIG. 1 illustrates the high level architecture of the system 100 which includes a user (e.g., patient) interfacing device 102 and a health care provider ("provider") interfacing device 104. As shown in FIG. 1, each of these interfacing devices (102, 104) includes one or more of the following components: a video capturing device 106 (e.g., a web camera or the like), an audio capturing device 108 (e.g., a microphone or the like), an audio and video displaying device 110 (e.g., a computer monitor, a laptop or tablet's screen display, or the like), a network communication device 112 (e.g., wired and wireless modems, network cards, Wi-Fi devices, Bluetooth devices, etc.), an interfacing device processor 138 and an interfacing memory 139. The interfacing memory 139 stores instructions which when executed by the interfacing device processor 138 causes the interfacing processor 138 to perform operations instructed by the frontend application (i.e., the user frontend application 118 or the provider frontend application 124). Moreover, the frontend applications (118, 124) may form a computer program product comprising a non-transitory computer-readable storage medium having computer-readable program code embodied therewith, the computer-readable program code configured to perform the operations as described in this specification.

It should be noted that the present invention also includes embodiments whereby some of these components (106, 108, 110, 112) are not all incorporated into a single physical device, but instead are either individual physical devices or be combined into two or more physical devices. In one exemplary embodiment, these interfacing devices (102, 104) can be any art-disclosed electronic devices such as a computer (e.g., laptop, desktop, or the like), a tablet, a smartphone, a virtual reality headset (e.g., Oculus Quest or Go; Sony PlayStation VR; HTC Vive Pro, etc.), or the like.

During operation, the interfacing devices (102, 104) run their respective frontend applications (118, 124) enabling the user interface 114 and the provider interface 120 accessed via the user internet browser 116 and the provider internet browser 122 to send, receive, and/or share (collectively hereinafter referred to as "communicate"): (a) at least one video data stream and audio data stream during the ARPT using Twilio video chat API, an equivalence such as WebRTC, Pubnub, TokBox, or the like (hereinafter collectively referred to "interactive communication API" 192) over a network 119; and (b) at least one data stream via Twilio DataTrack API, an equivalence such as a web socket, or a web socket interface such as socket.io or the like (collectively hereinafter referred as "data communication API" 194) over the network 119. The video stream sends and receives video data 126 between the user interface 114 and the provider interface 120, and the frontend applications (118, 124) render the video data 126 for the user and the provider to see. The audio stream sends and receives audio data 128 between the user interface 114 and the provider interface 120, and the frontend applications (118, 124) render the audio data 128 for the user and the provider to hear. The data stream sends and receives additional data 130 between the user interface 114 and the provider interface 120 via their respective internet browsers (116, 122) and the frontend applications (118, 124).

The frontend applications (118, 124) are also connected to a central server 132 (e.g., a HTTP server, Node.js server, a Firebase server, or the like) that handles all data transmission 134. The data transmission 134 is accomplished via art-disclosed browser-server protocols such as HTTP (Hypertext Transfer Protocol), FTP (File Transfer Protocol), FILE, or the like. The central server 132 communicates via art-disclosed means (e.g., a message-based protocol supported over TCP/IP and UNIX-domain sockets) with at least one database 150 that stores desired application data 152 relating to the user, the provider, and the ARPT. The database 150 can be any art-disclosed suitable database including a PostgreSQL database or its equivalent (e.g. mySQL, MangoDB, etc.). Accordingly, the interfacing devices (102, 104) enable the interfaces (114, 120) to be rendered with the application data 152 and viewed in a user internet web browser 116 when the frontend applications (118, 124) send and receive the data transmission 134 from the central server 132. The database 150 stores the application data 152 which it receives and/or generates, in a memory 154 of the system 100 for future use. The memory 154 may include any suitable device in which various information of the system 100 may be stored. Accordingly, the memory 154 may include a non-transitory memory which may store information generated by the system 100 such as information related to the ARPTs, the user, the provider, the appointment schedules, the operating programs, applications, settings, history, and/or other information of the system 100.

The system 100 may optionally include one or more bioinformation sensing devices 140 such as Fitbit, Apple Watch, LG Watch, Samsung Gear or any smart device that collect the user's bioinformation data 142 such as heart rate, temperature, blood pressure, blood oxygen level, blood glucose level, electrocardiograph (ECG/EKG), or the like. The bioinformation sensing device(s) 140 send the bioinformation data 142 to either (i) a companion bioinformation application 144 of the user's bioinformation receiving device 146 (e.g., computer, smartphone, tablet or the like), which then sends the bioinformation data 142 to a bioinformation server 148; or (ii) directly to the bioinformation server 148. The present invention includes the embodiments that allow the bioinformation sensing device 140, the bioinformation receiving device 146, and the user interfacing device 102 to be separate physical devices or entirely be incorporated into a single physical device. Moreover, the central server 132 may also function as the bioinformation server 148.

The system 100 provides for either the bioinformation sensing device 140 and/or the bioinformation receiving device 146 to send the bioinformation data 142 to one or more of the following components of the system 100 for processing and use: the bioinformation server 148, the user frontend application 118, the provider frontend application 124, and the center server 132. For example, the bioinformation sensing device 140 can directly send the bioinformation data 142 to the user frontend application 118 wherein such data 142 can be processed and sent to the center server 132 and the provider frontend application 124.

As discussed in detail below in the AR process 400, the system 100 uses the video capturing device 106 and the user frontend application 118 to capture and track the user's body motions derived from the video data 126 of the user live stream 166 during the ARPT in order to provide the captured body motion frame data 156. The user live stream 166 is comprised of the video data 126 and the audio data 128 being communicated between the user interface 114 and the provider interface 120 during the ARPT. The captured body motion frame data 156 is then analyzed using a pose detection model 196 such as PoseNet API, any art-disclosed vision machine learning model for real-time human pose estimation, or any real-time human pose estimation equivalence that can be built using machine learning library like Tensorflow, pytorch, keras, etc. (collectively hereinafter referred to as "pose detection model" 196) in order to produce the analyzed body motion frame data 157, which is sent back to the user frontend application 118. The user frontend application 118 then uses the analyzed body motion frame data 157 and p5.js, a JS client-side library, or an equivalence snap.svg, fabric.js, paper.js, d3.js, etc. (collectively referred to as "pose rendering library" 198) to assist the user by rendering a superposed skeleton image 206 on the user body image 208 shown in the user live stream 166 to create an augmented reality experience.

The system 100 optionally provides for appointment scheduling for the ARPTs using the user and provider frontend applications (118, 124), the central server 132 and the database 150. The process of how the system 100 provides for appointment scheduling is described below in the AR process 400 including the authenticating process 402, the scheduling process 404 and the appointment process 406.

The system 100 may optionally provide a language translation feature by having the frontend applications (118, 124) connect to a translation server 158 and to send the audio data 128 to the translation server 158. This translation feature by the system 100 is described below as the translation process 516.

The frontend applications (118, 124) form the client-side of the system 100 and communicate with the server-side of the system 100 (e.g., 132, 148, 158). All servers (132, 148, 158) discussed here may each include one or more processors 136 which is usually situated remotely (but also can be situated locally if desired) from each other. For example, the central server 132 includes one or more processors 136 which may be situated locally and/or remotely from each other and may control the overall operation of the system 100. Operations performed by the server processor(s) 136 are performed using one or more processors, logic devices, or the like. It should be noted that processes performed by the processors 136 can also be performed jointly or separately by interfacing device processors 138 located within the user interfacing device 102 and/or the provider interfacing device 104.

The network 119 may include one or more networks and may enable communication between or more components of the system 100 such as the interfacing devices (102, 104) the servers (132, 148, 158), the database 150, the bioinformation sensing and receiving devices (140, 146), etc. using any suitable transmission scheme such as wired and/or wireless communication schemes. Accordingly, the network 119 may include one or more networks such as a wide area network (WAN), a local area network (LAN), the Internet, a telephony network, (e.g., a public switched telephone network (PSTN), a 3G network, a 4G network, a 5G network, a code division multiple access (CDMA) network, a global service for mobile (GSM) network, a plain old telephone service (POTs) network, etc.), a peer-to-peer (P2P) network, a wireless fidelity (Wi-Fi™) network, a Bluetooth™ network, a proprietary network, and or other communication networks.

The Augmented Reality Physical Therapy Process

Figure 2:
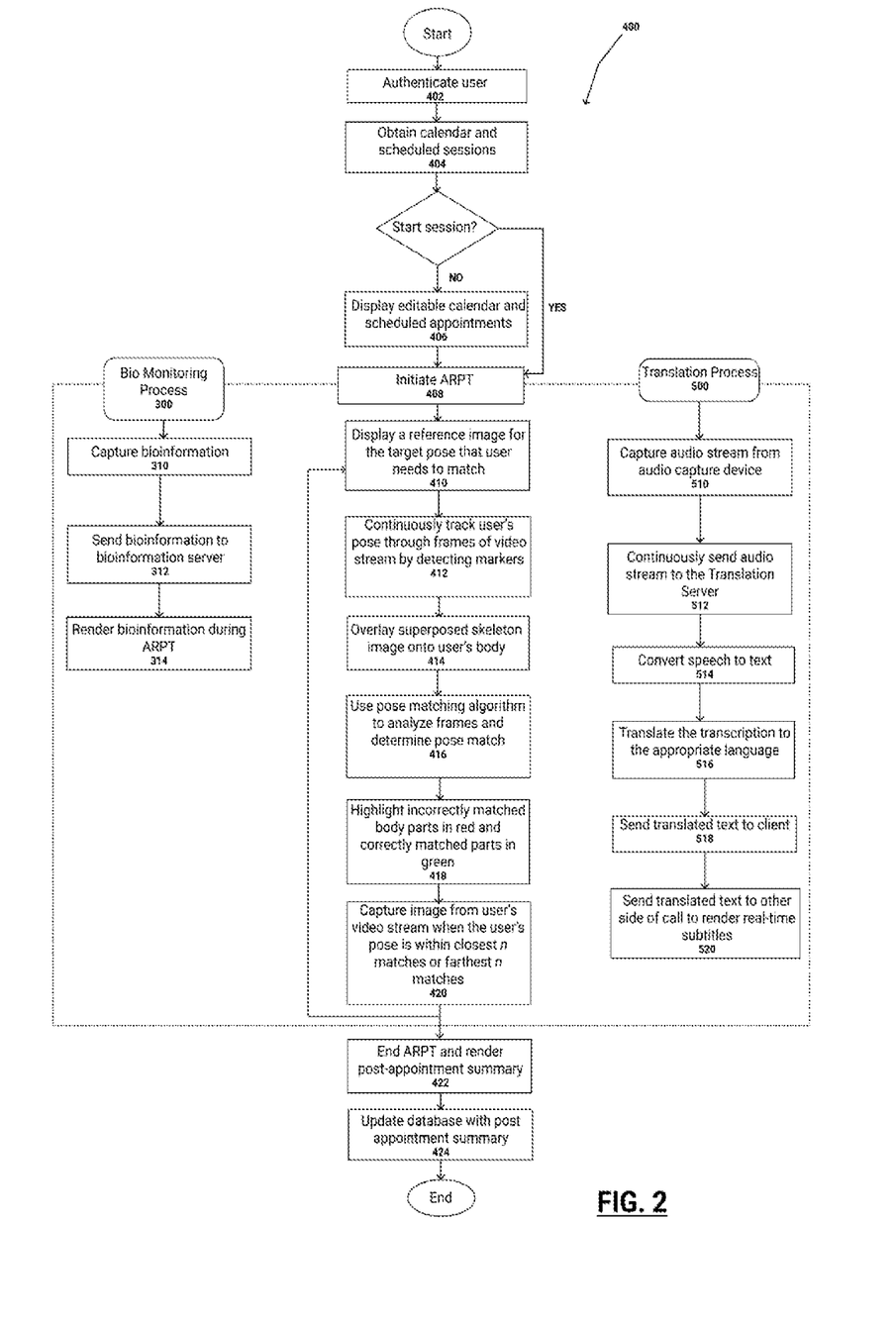
FIG. 2 is a flow diagram illustrates a process in accordance with embodiments of the present invention.

Referring to FIG. 1 and FIG. 2, the present invention also provides an AR process 400 using the system 100 to provide the ARPT. The AR process 400 includes an authenticating process 402. This process 402 requires the user, using Firebase Authentication API or an equivalent such as Auth0, MongoDB, Passport, Okta, etc., (hereinafter collectively referred to as "authentication API" 188) to create or logs into an existing account where his account data is stored in the database 150. During the authenticating process 402, a form is provided in the user interface 114 for inputting his credentials which are then sent to the central server 132 to be validated. Once the user's credentials are validated, the central server 132 will send an authentication token back to the user interface 114 so that the user may access his data from the database 150.

After the authenticating process 402, the AR process 400 further includes an optional scheduling process 404 whereby the user can view the provider's availability and scheduled sessions data, which is stored in the database 150, retrieved via the data transmissions 134 (e.g., HTTP requests) to the central server 132 and displayed on the user interface 114. Using the provider interface 120, the provider can post her available session time slots on her account calendar (which is part of the provider scheduling data 164). The provider's availability is displayed on her account calendar using the FullCalendar.io API or an equivalence such as Google Calendar API, React-Calendar API, etc. (hereinafter collectively referred to as "calendar API" 190). When the user selects the provider, the provider's calendar/planner will be displayed with all her available session slot times to be selected.

Once the user can access the provider's availability and scheduled sessions data 164 via the user interface 114 during the scheduling process 404, the AR process 400 further includes an optional appointment process 406 whereby the user selects one or more of the provider's available session slots. In one exemplary embodiment of the AR process 400, the user's scheduling data 162 (e.g., scheduled ARPTs) is displayed in a list of upcoming appointments on the user interface 114. Moreover, the user will be prompted to fill out pre-session information, including his symptoms or any files he wishes to import. After the session event has been submitted by the user, the event will be displayed in both the provider's and user's calendars (which are part of user scheduling data 162 and the provider scheduling data 164) with all the pre-session information. The providers have the authorization access to reschedule all scheduled and unscheduled sessions. The users can also edit their own scheduled sessions. The users and the providers can also view their lists of upcoming sessions they respectably have scheduled. The user scheduling data 162 and the provider scheduling data 164 may be incorporated into and stored as part of the application data 152.

The AR process 400 includes an initiating ARPT process 408 whereby both the user and the provider can "join now" to a scheduled ARPT using their user and provider interfaces (114, 120). This process 408 is achieved by the frontend applications (118, 124) using their respective interfacing devices (102, 104) with the video capturing devices 106 and the audio capturing devices 108, the interactive communication API 192, and the data communication API 194 to allow the user and the provider to be connected in this ARPT remote video session where they can send the video data 126, the audio data 128, and the additional data 130 to each other. After the initiating ARPT process 408, all of the processes described below and shown within the dashed-line box in FIG. 2 can be executed independently and therefore could occur in parallel.

Figure 3:
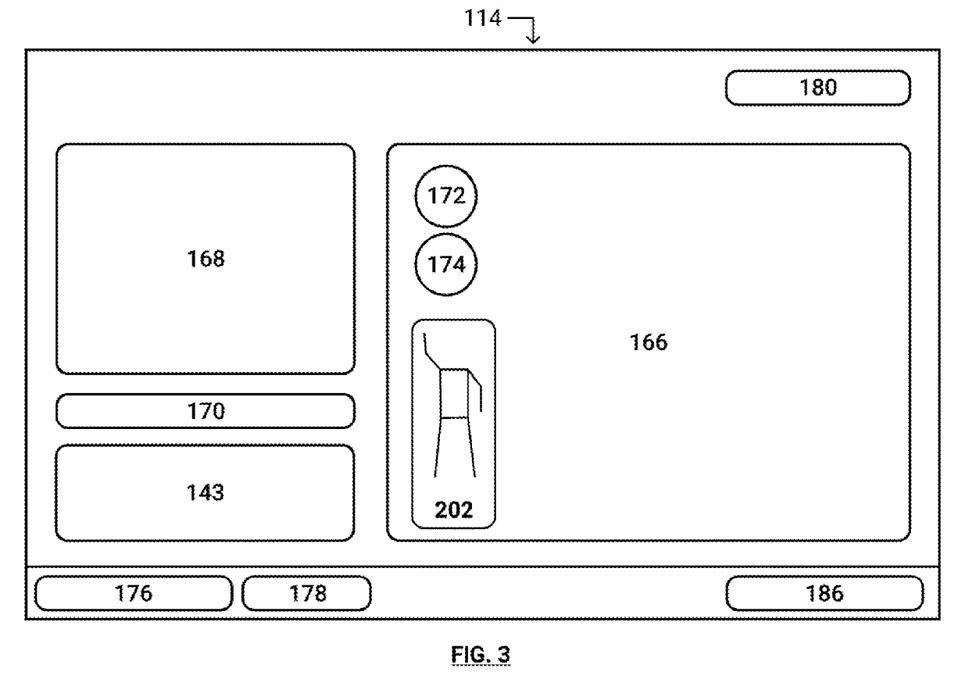
FIG. 3 is a diagram of an exemplary embodiment of the user interface of the augmented-reality system during a guided augmented reality physical therapy in accordance with embodiments of the present invention.
Figure 4:
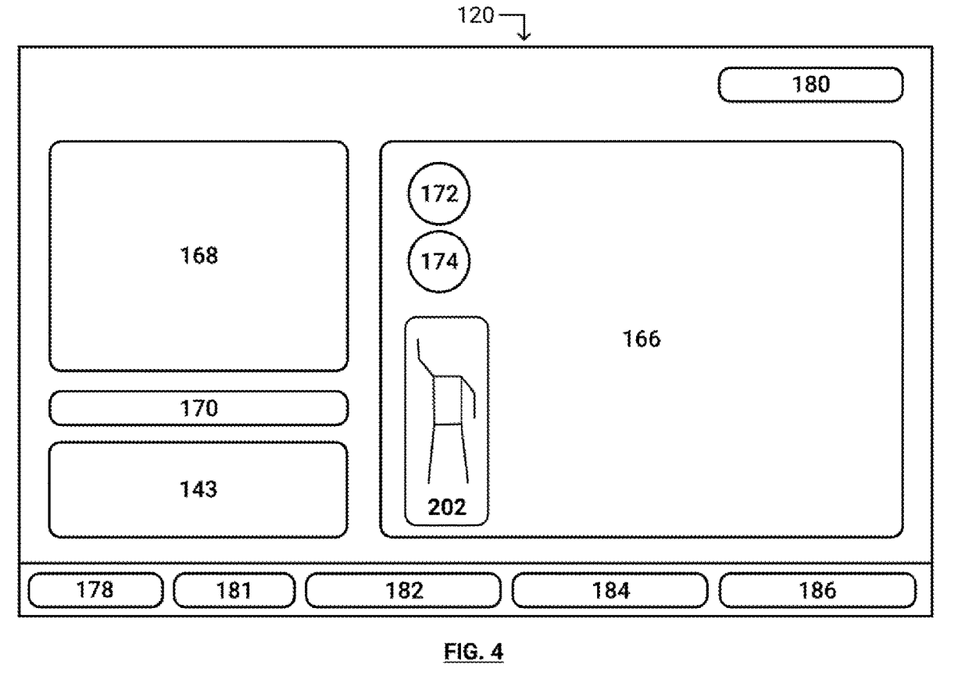
FIG. 4 is a diagram of an exemplary embodiment of the provider interface of the augmented-reality system during a guided augmented reality physical therapy in accordance with embodiments of the present invention.

The AR process 400 includes selecting an exercise process 410 whereby either the provider or (optionally) the user selects an exercise including the exercise's intensity level for the user to perform via his/her respectively frontend application (118 or 124) and a reference skeleton image 202 showing the target pose(s)/movement(s) (hereinafter referred to as "target pose(s)", which are rendered on at least the user interface 114 as shown in FIG. 3 in order to guide the user on how to perform the exercise. During the ARPT, the user should mimic the target poses shown as the reference skeleton image 202 and the provider can provide additional guidance to the user via the provider live stream 168, which is shown on the interfaces (114, 120). The provider live stream 168 is part of the video data 126 and the audio data 128 communicated between the provider and the user during the ARPT. The reference skeleton image 202 is also optionally provided on the provider interface 120 as shown in FIG. 4. To aid the selection of exercise(s) during this selection process 410, either the provider and/or the user may optionally access via his/her respective frontend application (118 or 124) the application data 152 relating to the user including prior medical history, data relating to the ARPT (e.g., bioinformation, types of exercises done, how well the exercises were performed, etc.) gathered from previous appointments can also aid the exercise selection process.

Once the reference skeleton image 202 is displayed on the user interface 114, the AR process 400 includes a motion tracking process 412 whereby the system 100 uses the video capturing device 106 and the user frontend application 118 to capture and track each video frame of the user's body poses/motions derived from the video data 126 of the user live stream 166 during the ARPT (hereinafter referred to as "user pose(s)") in order to provide the captured body motion frame data 156. The motion tracking process 412 further includes having the captured body motion frame data 156 analyzed by the pose detection model 196 to detect various locations of the user's body parts/joints (hereinafter referred to as "marker(s)" 204) in real-time thereby creating the analyzed body motion frame data 157, which is sent back to the user frontend application 118 (and optionally the provider frontend application 124) for further processing during a movement matching process 416 discussed below.

Figure 5:
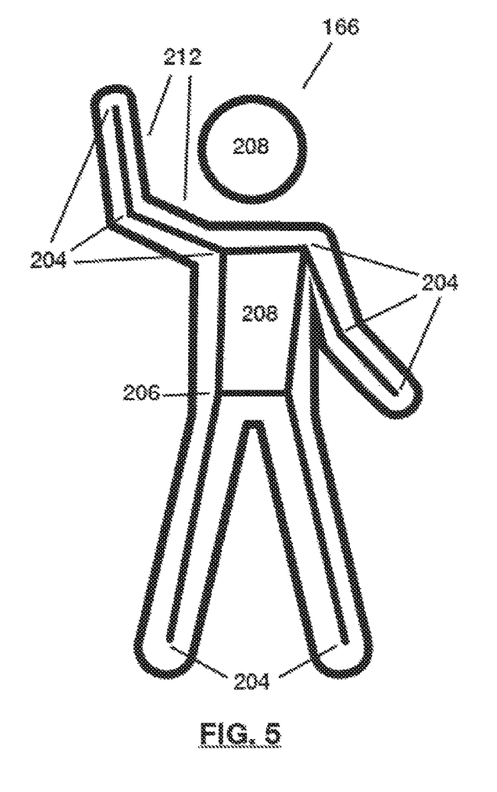
FIG. 5 is diagram illustrating the user live video feed with the superposed skeleton image displayed in the user interface as shown in FIG. 3 when the user is doing an exercise correctly.
Figure 6:
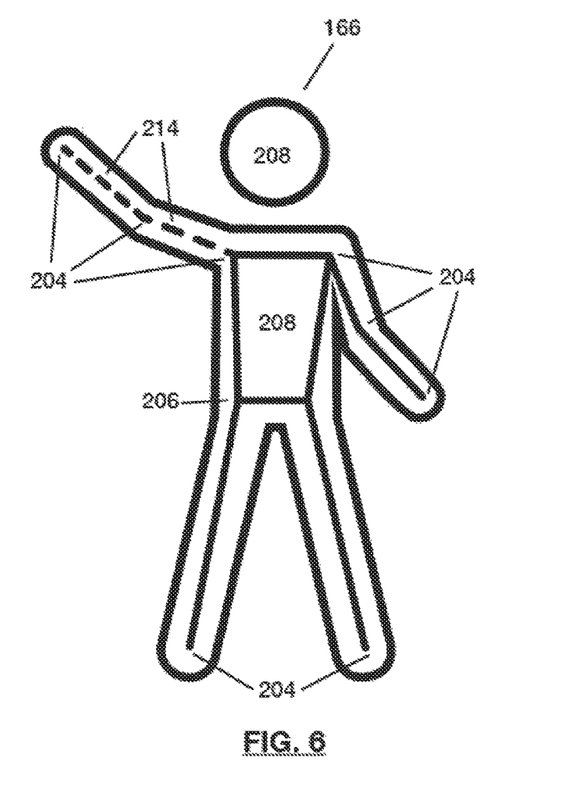
FIG. 6 is a diagram illustrating the user live video feed with the superposed skeleton image displayed in the user interface as shown in FIG. 3 when the user is doing an exercise incorrectly.

Referring to FIGS. 5 and 6, the marker 204 can be any desired body part/joint such as right shoulder, left shoulder, right elbow, left elbow, right wrist, left wrist, right hip, left hip, right knee, left knee, right ankle, left ankle, right rotator cuff, left rotator cuff, and other smaller joints such as finger joints, etc. Furthermore, the marker 204 can also be the mouth, ears, and/or eyes. Using the marker 204, groupings of markers can also be created that represent body parts. For example, the right arm is represented by the right shoulder, right elbow, and right wrist. We can define any body part as any grouping of markers 204. We also create a "body part" that includes all the markers 204 (e.g., entire body). This body part of the entire body is used later in the pose matching algorithm, in addition to the individual groupings like right arm, left arm, right leg, left leg, shoulders, hips, etc. Except for the body part consisting of the entire body, the correctness of each of the body parts is independent of each other. For example, the right arm is independent of the left arm.

The analyzed body motion frame data 157 output by the pose detection model 196 includes an (X, Y) coordinate for each marker 204 and a confidence score 210 for each coordinate. As explained below, the confidence scores 210 are then used during the movement matching process 416 for pose matching when evaluating whether the user poses have matched the target poses shown in the reference skeleton image 202.

The AR process 400 also provides for an image superposing process 414 whereby the user frontend application 118 (and optionally the provider frontend application 124) uses the pose rendering library 198 and the analyzed body motion frame data 157 to create and overlay a superposed skeleton image 206 onto the user body image 208 shown in the user live stream 166. The image superposing process 414 allows the superposed skeleton image 206 to dynamically tracks and moves with the movements of the user's markers 204. To create each frame of the superposed skeleton image 206, the X and Y coordinates of all of the markers 204 of the analyzed body motion frame data 157 are collected and adjusted based on the bounding box of the user pose. These X and Y coordinates assume (0,0) is at the base of each frame of the user live stream 166 and the bounding box of the user pose is calculated by finding the minimum X and Y coordinate of the analyzed body motion frame data 157 and translate each point.

So, a point $X_n$ becomes $(X_n - minX)$ and a point $Y_n$ becomes $(Y_n - minY)$ For each grouping of markers 204 defined as a body part discussed above (e.g., right arm, left arm, right leg, left leg, shoulders, hips, entire body, etc.), the image superposing process 414 uses the following pose matching algorithm: going in alphabetical order, by marker 204 for n markers 204 in a body part, the X and Y coordinates are added to a vector A (i.e., vector A for a specific body part) as shown below:

$A = [X_1, Y_1, X_2, Y_2, X_3, Y_3, \ldots X_n, Y_n]$

The vector A becomes a dimensional vector (i.e., 2n elements in the vector). Thereafter, the vector A is normalized using L2 normalization by dividing every element by the magnitude of the vector. For example, the vector A becomes vector L (L2 normalized vector for a specific body part)

$A = [X_1, Y_1, X_2, Y_2 \ldots X_n, Y_n]$ $$\text{Magnitude} = |A| = \sqrt{\sum_{k=1}^{n} A_k^2}$$

$$L = \left[ \frac{X_1}{|A|}, \frac{Y_1}{|A|}, \frac{X_2}{|A|}, \frac{Y_2}{|A|} \ldots \frac{X_n}{|A|}, \frac{Y_n}{|A|} \right]$$

"k" is an index of the summation, which goes from 1, the lower limit of summation, to n, the upper limit of summation. Each frame of the user live stream 166 is analyzed to generate the vector A and the vector L. As discussed below, the L is then used to calculate a similarity score to decide if the user is doing the exercise correctly (i.e., if the user poses match the target poses) by having a set of L vectors of various body parts (hereinafter referred to as "$S_1$") (e.g., $S_1 = \{L_{whole\ body}, L_{right\ arm}, L_{left\ arm}, L_{right\ leg}, \text{etc.} \ldots\}$).

The creation of target poses shown in the reference skeleton image 202 is accomplished using the same processes discussed above. The only difference is that the user is now the "reference" user who can perform the exercise(s) in a correct manner. The system 100 uses the video capturing device 106 and the user frontend application 118 to capture and track each video frame of the reference user doing an exercise correctly during the reference user live stream 166 in order to provide the captured body motion frame data 156. This data 156 is then analyzed by the pose detection model 196 to detect the reference user's markers 204 in real-time thereby creating the analyzed body motion frame data 157. This analyzed body motion frame data 157 includes an (X, Y) coordinate for each marker 204 and a confidence score 210 for each coordinate. The analyzed body motion frame data 157 is sent back to the user frontend application 118 where it is processed by the pose rendering library 198 to create the target poses shown in the reference skeleton image 202. To create each frame of the target poses shown in the reference skeleton image 202, the X and Y coordinates of all of the markers 204 of the analyzed body motion frame data 157 are collected and adjusted by the user frontend application 118 based on the bounding box of the target pose. These X and Y coordinates assume (0,0) is at the base of each frame of the user live stream 166 and the bounding box of the target pose is calculated by finding the minimum X and Y coordinate of the analyzed body motion frame data 157 and translate each point.

So, a point $X_n$ becomes $(X_n-minX)$ and a point $Y_n$ becomes $(Y_n-minY)$

For each grouping of markers 204 defined as a body part discussed above (e.g., right arm, left arm, right leg, left leg, shoulders, hips, entire body, etc.), the image superposing process 414 uses the same pose matching algorithm discussed above (for clarification purposes, this reference vector is shown below as "B" (i.e., vector B for a specific body part): going in alphabetical order, by marker 204 for n markers 204 in a body part, the X and Y coordinates are added to the vector B as shown below:

$B=[X_1, Y_1, X_2, Y_2, X_3, Y_3, \ldots X_n, Y_n]$

The vector B becomes a 2n dimensional vector and is subsequently normalized using L2 normalization by dividing every element by the magnitude of the vector B and becomes vector R:

$$B = [X_1, Y_1, X_2, Y_2 \ldots X_n, Y_n]$$

$$\text{Magnitude} = |B| = \sqrt{\sum_{k=1}^{n} A_k^2}$$

$$R = \left[\frac{X_1}{|B|}, \frac{Y_1}{|B|}, \frac{X_2}{|B|}, \frac{Y_2}{|B|} \ldots \frac{X_n}{|B|}, \frac{Y_n}{|B|}\right]$$

"k" is an index of the summation, which goes from 1, the lower limit of summation, to n, the upper limit of summation. Each frame of the reference user live stream 166 is analyzed to generate the vector B and the vector R. As discussed below, the vector R is later used to calculate a similarity score to decide if the user is doing the exercise correctly (i.e., if the user poses match the target poses) by having a set of R vectors "$S_2$" (e.g., $S_2=\{R_{whole\ body}, R_{right\ arm}, R_{left\ arm}, R_{right\ leg}$, etc. . . . \}). The vectors $S_2$ are stored in the frontend application 118 for later use to compare with the user poses. It is optional but preferred to create a set of multiple R vectors per body part in an effort to account for slight variances in position (e.g., movements).

In order to ensure that the user's body shape and size are properly considered and evaluated during the AR process 400, the image superposing process 414 uses the above-described normalization process to compare the bounding box around the user pose's markers 204 to the bounding box around the target pose's markers 204. This comparison results in a factor that the system 100 must scale the user pose's markers 204 in order to match the target pose's markers 204. The bounding box discussed herein is the smallest possible rectangle that encloses all of the markers 204 contained within a pose. Since the user pose and the target pose have their own respective markers 204, they also have their own respective bounding boxes.

During the motion tracking process 412 and the image superposing process 414, the AR process 400 further provides for a movement matching process 416 whereby the user frontend application 118 (and optionally the provider frontend application 124) also uses the pose matching algorithm to determine whether the corresponding target poses shown in the reference skeleton image 202 have been matched by the user poses shown in the superposed skeleton image 206. As discussed above, during the AR process 400, every frame of the user poses shown in the superposed skeleton image 206 is analyzed to generate $S_1$ (the set of L vectors) for comparison with the corresponding $S_2$ (the set of R vectors). The pose matching algorithm is implemented by comparing the two sets of normalized vectors:

$$\text{Similarity Score} = \frac{1}{\sum_{k=1}^{n} C_k} \times \sum_{k=1}^{2n} C_k \cdot |L_k - R_k|$$

or slightly simplified:

$$\text{Similarity Score} = \frac{1}{\sum_{k=1}^{n} C_k} \times \sum_{k=1}^{n} C_k \cdot |L_k - R_k|$$

Where $C_k$ is the confidence score 210 at the $k^{th}$ element, and $L_k$ and $R_k$ are the $k^{th}$ elements in the respective vectors.

Initially, it is preferred that the movement matching process 416 uses the similarity scores derived from comparing the L and the corresponding set of R vectors for whole body. Moreover, when the kth element is the whole body, then $C_k$ is a vector of the user's confidence scores 210: $C_k=[C_1, C_2, C_3, \ldots C_n]$. The reference user's confidence scores 210 are assumed to be at 100 percent thus not used in the similarity score calculation. An average of these similarity scores across all the reference vectors for a given frame in a stage of an exercise is calculated. These similarity scores determine whether the user pose is matching the target pose (i.e., whether the user is doing the exercise correctly). The closer the similarity score is to 0, the more similar the two $L_k$ and $R_k$ vectors are. If the similarity score for a predetermined number of frames is under a predetermined target threshold, then the user is doing the exercise correctly.

Meeting the target threshold means that there is a correct execution of the exercise by the user—basically, the user pose sufficiently matches the target pose shown in the reference skeleton image 202 for a desired duration of time (hereinafter referred to as "target threshold"). The provider can set the target threshold. For example, if the provider is being lenient, the threshold can be set to 0.09, while medium is set to 0.08 and strict is set to 0.07, etc.

During the motion tracking process 412, the image superposing process 414, and the movement matching process 416, the AR process 400 further provides for a movement alerting process 418 whereby if the similarity score for a predetermined number of frames is under or within the target threshold, then the system 400 renders that certain markers 204 for specific body part(s) of the superposed skeleton image 206 a particular color 212 (e.g., green and shown in FIG. 5 as a solid line). Otherwise, the system 400 renders such markers 204 of the superposed skeleton image 206 a different color 214 (e.g., red and shown in FIG. 6 as a dashed line). For example, in one exemplary embodiment, in order to get color 212, the user pose shown in the superposed skeleton image 206 must meet the match target threshold of having the similarity score to be less than 0.07 and having such "correct" pose held for at least 5 frames. The system 100 further optionally allows the provider to adjust the requirement/strictness of the target threshold by setting the cosine similarity to be a specific level (e.g., <0.07 for strict, <0.08 for medium, <0.09 for lenient) and/or the duration of the "correct" pose (e.g., >5 frames, >10 frames, >30 frames, etc.).

If the user is in the correct pose for a given number of frames consecutively (e.g., ≥5 frames), the user pose is considered matched to the target pose, and the reference image shifts to the next stage of the exercise. If it is at the end position of a particular movement, the user is said to have completed a repetition, and the repetition count 174 discussed below is updated. If the user is not in the correct pose for the whole body, then need to show the user which portion of his body (i.e., specific individual body part) is in an incorrect pose/position. As discussed above, the L and R vectors, along with the similarity scores are obtained for each of the individual body parts so the AR process 400 can also uses the same target threshold to determine the correctness of each of the individual body parts' pose/position.

During the movement alerting process 418, the system 100 using the user frontend application 118 optionally counts and displays on the interfaces (114, 120) the number of repetitions of the exercise completed by the user matching the target pose (i.e., correct execution of the exercise and hereinafter referred to as "correct repetition count" 172). The system 100, using the user frontend application 118, also optionally counts and displays on the interfaces (114, 120) the total number of repetitions of the exercise completed by the user during the ARPT (hereinafter referred to as "repetition count" 174).

Throughout the ARPT, the AR process 400 provides for a movement capturing process 420 wherein the closest or best n pose matches (i.e. how well the user poses matched the target poses) and the farthest or substandard n pose matches are continuously recorded and updated based on the user's performance. When a new closest/farthest pose match is found, the user live stream 166 is captured (along with the superposed skeleton image 206), so that it can be made available for viewing by the user and the provider after the ARPT.

The the ARPT, the AR process 400 optionally provides a reviewing process 422 wherein both the provider and the user can see a summary of the application data 152 collected during the ARPT. This summary includes but is not limited to the following application data 152: the user's heart rate graph, maximum heart rate, completed repetitions, screenshots of the user's closest/farthest pose matches, and any other collected metrics may also be summarized. Moreover, the AR process 400 also optionally provides an updating process 424 wherein the database 150 is updated with the application data 152 created during the reviewing process 422 for viewing at a later time.

During the ARPT, the AR process 400 may optionally include a biomonitoring process 300 comprising of the following processes. The acquiring bioinformation process 310 occurs when the user initiates the bioinformation sensing device 140 (e.g., wearable heart rate monitor) in order to acquire his bioinformation data 142 (e.g., heart rate) during the ARPT. The sending bioinformation to server process 312 occurs when the bioinformation data 142 is send to the bioinformation server 148, either directly from the bioinformation sensing device 140 or via an intermediary such as the user interfacing device 102. The rendering bioinformation process 314 occurs when the user frontend application receives the bioinformation data 142 from the bioinformation server 148 and renders the bioinformation data 142 for use and incorporation into the user interface 114 and/or the provider interface 120. The bioinformation data 142 is processed in real time by the user's front end application 118 where such data 142 is converted into a live chart and/or big number (hereinafter referred to as "bioinformation chart" 143). The provider, with the aid of the provider frontend application 124, can use the bioinformation data 142 to make real-time suggestions to the user during the ARPT for the user's physical health. For example, possible suggestions include slowing down the repetitions of the exercise if the user is clearly fatigued or in pain based on his heart rate. Moreover, the system 100 via the AR process 400 can alert the provider and the user of known health risks based on the vitals (e.g. heart rate abnormally high or the like). The provider can also suggest recovery plans, based on the user's bioinformation data 142. The bioinformation data 142 is incorporated into the application data 152 for processing and storage.

During the ARPT, the AR process 400 may optionally provide a language translating process 500 including the following processes. The audio capturing process 510 captures the audio data 128 of the client (e.g., the user and/or the provider) via his/her audio capturing device 108. The audio streaming process 512 continuously streams the captured audio data 128 to the translation server 158 via WebSocket (or other art-disclosed means such as HTTP/HTTPS, etc.) 200. Thereafter, the transcription process 514 occurs when the audio data 128 is forwarded to the GCP Speech-to-Text API or some speech recognition service such as Google Cloud Speech-to-Text, Amazon Transcribe, IBM Watson Speech to Text, or the like (hereinafter referred to as "transcription API" 160) which returns a text transcription of the input (hereinafter referred to as "transcribed text" 169). Subsequently, the translating process 516 occurs when the transcribed text 169 is sent to the Google Translate API or an equivalent translation API such as Google Translate, Amazon Translate, Microsoft Translation, or the like (collectively hereinafter referred to as "translation API" 163) and translated to the target language text (hereinafter referred to "translated text" 170). The target language is the language desired by the receiver (either the user or the provider) at the other end of the ARPT and is pre-set in his/her preferences (and/or selected via the translation menu 176 shown in FIG. 3). The translated text 170 is sent back to the client's internet browser (116 or 122) by the translation server 158 during the client receiving process 518. Finally, during the translation receiving process 520, the translated text 170 is sent by the frontend application (118 or 124) to the other frontend application (124 or 118) via Twilio DataTrack API, a web socket, or a web socket interface such as socket.io or the like (collectively hereinafter referred as "communication API" 194). Each chunk of the translated text 170 received is rendered as a subtitle of the caller's (either the user or the provider) speech in real-time on his/her interface (114 or 120).

The system 100 and the AR process 400 can be used for purposes other than providing guided augmented-reality physical therapy to the user. Instead, The present invention with the system 100 and the AR process 400 described above can also be used for the provider (e.g., instructor, trainer, or the like) to guide the user to perform any form of physical exercise such as physical fitness training, yoga, dance, basketball movements, golf club swings, baseball bat swings, baseball throws, etc.

The User Interface and the Provider Interface During ARPT

Referring to FIG. 3, during an ARPT, the user interface 114 shown on the audio and video display 110 of the user interfacing device 102 may show one or more of the following features: an identification profile 180 identifying the individual using the interface (e.g., name, photo, avatar, etc.); the user live stream 166; the provider live stream 168; a bioinformation menu 178 (e.g., heart rate, etc.) that activates or deactivates the biomonitoring process 300; the bioinformation chart 143; the translated text 170; the reference skeleton image 202; the superposed skeleton image 206 (overlaid onto the user body image 208 shown on the user live stream 166); the correction repetition count 172; the repetition count 174; a translation menu 176 that activates/deactivates the translation process 500 and selects the desired target language text; a session menu 186 that activates/deactivates the ARPT session. Referring to FIG. 4, during an ARPT, the provider interface 120 shown on the a display 110 of the provider interfacing device 104 may show one or more of the following features: the identification profile 180; the user live stream 166; the provider live stream 168; the bioinformation chart 143; the translated text 170; the reference skeleton image 202; the superposed skeleton image 206; the correction repetition count 172; the repetition count 174; an exercise menu 181 that activates or deactivates the selected exercise; the session menu 186; an exercise selection menu 182 that allows the individual to select a pre-programmed exercise; the exercise intensity menu 184 that allows the individual to select the target intensity (e.g., speed, etc.) of the exercise. The provider interface 120 may optionally provide the translation menu 176; and other menus relating to the bioinformation data 142, the user scheduling data 162, the provider scheduling data 164, and/or any other information relating to the ARPT. Similarly, the user interface 114 may optionally provide the exercise selection menu 182, the exercise intensity menu 184, and other menus relating to the bioinformation data 142, the user scheduling data 162, the provider scheduling data 164, and/or any other information relating to the ARPT.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled.

The disclosures of all articles and references, including patent applications and publications, are incorporated by reference for all purposes. Other combinations are also possible as will be gleaned from the following claims, which are also hereby incorporated by reference into this written description.

Example I

In this example, the AR Process 400 uses the above-discussed and shown below pose matching algorithm and an exemplary set of both the user pose and the corresponding target pose's analyzed body motion frame data 157 to determine if the user pose matches the target pose.

Pose Matching Algorithm:

$$A = [X_1, Y_1, X_2, Y_2 \ldots X_n, Y_n]$$

$$\text{Magnitude} = |A| = \sqrt{\sum_{k=1}^{n} A_k^2}$$

$$L = \left[\frac{X_1}{|A|}, \frac{Y_1}{|A|}, \frac{X_2}{|A|}, \frac{Y_2}{|A|} \ldots \frac{X_n}{|A|}, \frac{Y_n}{|A|}\right]$$

$$B = [X_1, Y_1, X_2, Y_2 \ldots X_n, Y_n]$$

$$\text{Magnitude} = |B| = \sqrt{\sum_{k=1}^{n} A_k^2}$$

$$R = \left[\frac{X_1}{|B|}, \frac{Y_1}{|B|}, \frac{X_2}{|B|}, \frac{Y_2}{|B|} \ldots \frac{X_n}{|B|}, \frac{Y_n}{|B|}\right]$$

$$\text{Similarity Score} = \frac{1}{\sum_{k=1}^{n} C_k} \times \sum_{k=1}^{n} C_k \cdot |L_k - R_k|$$

TABLE I

The analyzed body motion frame data 157

| Body Part | $X^a$ | $Y^a$ | User's Confidence Score 210 | $X^b$ | $Y^b$ | $X^c$ | $Y^c$ | $X^d$ | $Y^d$ |
|---|---|---|---|---|---|---|---|---|---|
| Left elbow | 6 | 4 | 0.90 | 5 | 3 | 6 | 4 | 5 | 3 |
| Left hip | 5 | 3 | 0.80 | 4 | 2 | 5 | 3 | 4 | 2 |
| Left knee | 5 | 1 | 0.80 | 4 | 0 | 5 | 1 | 4 | 0 |
| Left shoulder | 5 | 6 | 0.85 | 4 | 5 | 5 | 6 | 4 | 5 |
| Left wrist | 6 | 3 | 0.90 | 5 | 2 | 6 | 3 | 5 | 2 |
| Right elbow | 1 | 7 | 0.90 | 0 | 6 | 2 | 8 | 1 | 7 |
| Right hip | 3 | 3 | 0.80 | 2 | 2 | 3 | 3 | 2 | 2 |
| Right knee | 3 | 1 | 0.50 | 2 | 0 | 3 | 1 | 2 | 0 |
| Right shoulder | 3 | 6 | 0.90 | 2 | 5 | 3 | 6 | 2 | 5 |
| Right wrist | 1 | 10 | 0.90 | 0 | 9 | 1 | 10 | 0 | 9 |

$X^a$ and $Y^a$ are coordinates for the markers 204 of the user pose. $X^b$ and $Y^b$ are adjusted coordinates for the markers 204 based upon the user pose' bounding box wherein the X and Y minimum values are calculated in this case with minX=1, and minY=1. $X^c$ and $Y^c$ are coordinates for the markers 204 of the target pose. $X^d$ and $Y^d$ are adjusted coordinates for the markers 204 based upon the target pose' bounding box wherein the X and Y minimum values are calculated in this case with minX=1, and minY=1.

For the whole body, the confidence score vector $C_k$ is calculated using the user's confidence scores 210 as shown herein:

$C_{whole\ body}$=[0.9, 0.9, 0.9, 0.9, 0.9, 0.85, 0.8, 0.8, 0.5, 0.8].
Vector $A_{whole\ body}$ and vector $B_{whole\ body}$ are calculated with all of the X and Y coordinates of the markers 204 alphabetized (as shown in Table 1):

$A_{whole\ body}$=[5, 3, 4, 2, 4, 0, 4, 5, 5, 2, 0, 6, 2, 2, 2, 0, 2, 5, 0, 9]

Magnitude of $A_{whole\ body}$ (|A|) is 17.2626

$L_{whole\ body}$=[0.08389261744966447, 0.030201342281879210, 0.05369127516778526, 0.013422818791946315, 0.05369127516778526, 0, 0.05369127516778526, 0.08389261744966447, 0.08389261744966447, 0.013422818791946315, 0, 0.12080536912751684, 0.013422818791946315, 0.013422818791946315, 0.013422818791946315, 0, 0.013422818791946315, 0.08389261744966447, 0, 0.27181208053691286]

$B_{whole\ body}$: [5, 3, 4, 2, 4, 0, 4, 5, 5, 2, 1, 7, 2, 2, 2, 0, 2, 5, 0, 9]

Magnitude of $B_{whole\ body}$ (|B|) is 17.6635

$R_{whole\ body}$=[0.08012820512820511, 0.028846153846153844, 0.05128205128205127, 0.012820512820512818, 0.05128205128205127, 0, 0.05128205128205127, 0.08012820512820511, 0.08012820512820511, 0.012820512820512818, 0.0032051282051282046, 0.15705128205128202, 0.012820512820512818, 0.012820512820512818, 0.012820512820512818, 0, 0.012820512820512818, 0.08012820512820511, 0, 0.2596153846153845]

Similarity score for the whole body pose match: 0.00798694221513019. This is below any of the target thresholds discussed above (0.07, 0.08 or 0.09) so if the user holds this pose for the desired amount of time (e.g., 5 frames, etc.) consecutively, the pose will be considered matched resulting in the entire superposed skeleton image 206 being shown in color 212. If the similarity score for the whole body pose match is below the target threshold, then the user pose is considered as not matching the target pose. Under this scenario, the above pose matching algorithm process would be performed for each individual body part and/or each grouping of body parts (e.g., right arm would be defined as [right wrist, right elbow, and right shoulder), and the markers 204 of the non-matching body parts determined and shown in color 214 in the superposed skeleton image 206.

What is claimed is:

1. A computer implemented method to provide a guided augmented-reality physical exercise in a virtual platform ("ARPE") implemented in a system having a central server, a database, a user interfacing device, a provider interfacing device, each having one or more processors and a memory; the computer implemented method comprising executing on the one or more processors the steps of:
   initiating the ARPE wherein:
      a user uses the user interfacing device to communicate with a provider during the ARPE, wherein the user interfacing device further includes a user video capturing device, a user audio capturing device, and a user interface controlled by a user frontend application;
      the provider uses the provider interfacing device to communicate with the user during the ARPE, wherein the provider interfacing device further includes a provider video capturing device, a provider audio capturing device, and a provider interface controlled by a provider frontend application;
      the user interfacing device and the provider interfacing device are communicating video data and audio data via an interactive communication application programming interface (API) over a network wherein the video data includes a user live stream showing a user body image and user poses captured by the user video capturing device and displayed on the user interface and the provider interface;
   selecting a target exercise wherein a reference skeleton image is rendered and animated on the user interface by the user frontend application showing target poses, wherein the target poses demonstrate desired body movements of the target exercise thereby allowing user to mimic the target poses during the target exercise with the user poses;
   capturing and tracking the user poses during the target exercise using the user video capturing device and the user frontend application to provide captured body frame data for each video frame of the user live stream during the target exercise;
   analyzing the captured body frame data using a pose detection model to provide analyzed body motion frame data comprising markers and confidence scores, wherein the markers include two dimensional X and Y coordinates;
   creating a superposed skeleton image onto the user body image displayed on the user live stream using the user frontend application, a pose rendering library, and a pose matching algorithm to process the analyzed body motion frame data in order to obtain normalized vectors of the two dimensional X and Y coordinates, thereby allowing the superposed skeleton image to dynamically track and move with the user poses;
   determining whether the user poses match the target poses based upon similarity scores derived from the normalized vectors of the two dimensional X and Y coordinates and the confidence scores processed by the pose matching algorithm; and
   indicating whether a match exists between the user poses and the target poses by changing appearance of one or more portions of the superposed skeleton image.

2. The computer implemented method of claim 1 wherein if the user poses do not match the target poses, the one or more portions of the superposed skeleton image that are mismatched will change to a different color.

3. The computer implemented method of claim 1 wherein if the user poses match the target poses, the superposed skeleton image will not change in appearance and the user interface includes a display feature showing a number of matches performed by the user during the target exercise.

4. The computer implemented method of claim 1 wherein during the determining step, the user poses are considered matched to the target poses when the similarity scores for a predetermined number of video frames are greater or equal to a target threshold.

5. The computer implemented method of claim 4 wherein the target threshold is greater or equal to 0.7 similarity score for at least 5 video frames.

6. The computer implemented method of claim 1 wherein the computer implemented method further includes setting up an appointment for the ARPE using an authentication API, a calendar API, and the database.

7. The computer implemented method of claim 1 wherein the provider interface displays a feature selected from the group consisting of an identification profile, the user live stream, a provider live stream, a bioinformation chart, translated text, the reference skeleton image, the superposed skeleton image, a correction repetition count, an exercise selection menu that allows the provider to select a pre-programmed exercise, an exercise intensity menu that allows the provider to select a target intensity of the pre-programmed exercise, and a combination thereof.

8. The computer implemented method of claim 1 wherein the user interface displays a feature selected from the group consisting of an identification profile, the user live stream, a provider live stream, a bioinformation chart, translated text, the reference skeleton image, the superposed skeleton image, a correction repetition count, a a bioinformation menu that activates or deactivates a biomonitoring process, a bioinformation chart, a translation menu that activates or deactivates a translation process and selects a desired target language text, and a combination thereof.

9. The computer implemented method of claim 1 wherein the computer implemented method further includes translating the audio data into text in a pre-determined language during the ARPE using a transcription API and a translation API.

10. The computer implemented method of claim 1 wherein the computer implemented method further includes obtaining bioinformation data by the user frontend application during the ARPE using a bioinformation sensing device and a bioinformation server.

11. The computer implemented method of claim 1 wherein the target exercise performed during the ARPE is selected from the group consisting of: physical fitness training, yoga, dance, basketball movements, golf club swings, baseball bat swings, and baseball throws.

12. A non-transitory computer readable medium comprising computer-executable instructions that when executed by a processor perform a method of providing a guided augmented-reality physical exercise in a virtual platform ("ARPE") comprising:
   initiating the ARPE wherein:
   a user uses a user interfacing device to communicate with a provider during the ARPE, wherein the user interfacing device includes a user video capturing device, a user audio capturing device, and a user interface controlled by a user frontend application;
   the provider uses a provider interfacing device to communicate with the user during the ARPE, wherein the provider interfacing device includes a provider video capturing device, a provider audio capturing device, and a provider interface controlled by a provider frontend application;
   the user interfacing device and the provider interfacing device are communicating video data and audio data via an interactive communication application programming interface (API) over a network wherein the video data includes a user live stream showing a user body image and user poses captured by the user video capturing device and displayed on the user interface and the provider interface;
   selecting a target exercise wherein a reference skeleton image is rendered and animated on the user interface by the user frontend application showing target poses, wherein the target poses demonstrate desired body movements of the target exercise thereby allowing user to mimic the target poses during the target exercise with the user poses;
   capturing and tracking the user poses during the target exercise using the user video capturing device and the user frontend application to provide captured body frame data for each video frame of the user live stream during the target exercise;
   analyzing the captured body frame data using a pose detection model to provide analyzed body motion frame data comprising markers and confidence scores, wherein the markers include two dimensional X and Y coordinates;
   creating a superposed skeleton image onto the user body image displayed on the user live stream using the user frontend application, a pose rendering library, and a pose matching algorithm to process the analyzed body motion frame data in order to obtain normalized vectors of the two dimensional X and Y coordinates, thereby allowing the superposed skeleton image to dynamically track and move with the user poses;
   determining whether the user poses match the target poses based upon similarity scores derived from the normalized vectors of the two dimensional X and Y coordinates and the confidence scores processed by the pose matching algorithm; and
   indicating whether a match exists between the user poses and the target poses by changing appearance of one or more portions of the superposed skeleton image.

13. The non-transitory computer readable medium of claim 12 wherein if the user poses do not match the target poses, the one or more portions of the superposed skeleton image that are mismatched will change to a different color.

14. The non-transitory computer readable medium of claim 12 wherein if the user poses match the target poses, the superposed skeleton image will not change in appearance and the user interface includes a display feature showing a number of matches performed by the user during the target exercise.

15. The non-transitory computer readable medium of claim 12 wherein during the determining step, the user poses are considered matched to the target poses when the similarity scores for a predetermined number of video frames are greater or equal to a target threshold.

16. The non-transitory computer readable medium of claim 15 wherein the target threshold is greater or equal to 0.7 similarity score for at least 5 video frames.

17. The non-transitory computer readable medium of claim 12 wherein the method further includes setting up an appointment for the ARPE using an authentication API, a calendar API, and the database.

18. The non-transitory computer readable medium of claim 12 wherein the method further includes translating the audio data into text in a pre-determined language during the ARPE using a transcription API and a translation API.

19. The non-transitory computer readable medium of claim 12 wherein the target exercise performed during the ARPE is selected from the group consisting of: physical fitness training, yoga, dance, basketball movements, golf club swings, baseball bat swings, and baseball throws.

20. A non-transitory computer readable medium comprising computer-executable instructions that when executed by a processor perform a method of providing a guided augmented-reality physical exercise in a virtual platform ("ARPE") comprising:
   initiating the ARPE wherein:
   a user uses a user interfacing device to communicate with a provider during the ARPE, wherein the user interfacing device includes a user video capturing device, a user audio capturing device, and a user interface controlled by a user frontend application;
   the provider uses a provider interfacing device to communicate with the user during the ARPE, wherein the provider interfacing device includes a provider video capturing device, a provider audio capturing device, and a provider interface controlled by a provider frontend application;
   the user interfacing device and the provider interfacing device are communicating video data and audio data via an interactive communication application programming interface (API) over a network wherein the video data includes a user live stream showing a user body image and user poses captured by the user video capturing device and displayed on the user interface and the provider interface;

selecting a target exercise wherein a reference skeleton image is rendered and animated on the user interface by the user frontend application showing target poses, wherein the target poses demonstrate desired body movements of the target exercise thereby allowing user to mimic the target poses during the target exercise with the user poses;

capturing and tracking the user poses during the target exercise using the user video capturing device and the user frontend application to provide captured body frame data for each video frame of the user live stream during the target exercise;

analyzing the captured body frame data using a pose detection model to provide analyzed body motion frame data comprising markers and confidence scores, wherein the markers include two dimensional X and Y coordinates;

creating a superposed skeleton image onto the user body image displayed on the user live stream using the user frontend application, a pose rendering library, and a pose matching algorithm to process the analyzed body motion frame data in order to obtain normalized vectors of the two dimensional X and Y coordinates, thereby allowing the superposed skeleton image to dynamically track and move with the user poses;

determining whether the user poses match the target poses based upon similarity scores derived from the normalized vectors of the two dimensional X and Y coordinates and the confidence scores processed by the pose matching algorithm;

indicating whether a match exists between the user poses and the target poses by changing appearance of one or more portions of the superposed skeleton image;

obtaining bioinformation data by the user frontend application during the ARPE using a bioinformation sensing device and a bioinformation server; and translating the audio data into text in a pre-determined language during the ARPE using a transcription API and a translation API.

\* \* \* \* \*

UNITED STATES PATENT AND TRADEMARK OFFICE
CERTIFICATE OF CORRECTION

| | | |
|---|---|---|
| PATENT NO. | : 11,395,940 B2 | Page 1 of 1 |
| APPLICATION NO. | : 17/065303 | |
| DATED | : July 26, 2022 | |
| INVENTOR(S) | : Christopher Lee Lianides et al. | |

It is certified that error appears in the above-identified patent and that said Letters Patent is hereby corrected as shown below:

In the Claims

Column 17, Line 6 delete "a a bioinformation" and insert --a bioinformation--

Signed and Sealed this
Eighteenth Day of October, 2022

*Katherine Kelly Vidal*

Katherine Kelly Vidal
*Director of the United States Patent and Trademark Office*